United States Patent
Geist et al.

(10) Patent No.: US 9,339,309 B1
(45) Date of Patent: May 17, 2016

(54) SYSTEMS AND METHODS FOR INSERTING CROSS-CONNECTORS

(71) Applicant: NuVasive, Inc., San Diego, CA (US)

(72) Inventors: Wyatt Drake Geist, Davie, FL (US); Christopher Walsh, Jupiter, FL (US)

(73) Assignee: NuVasive, Inc., San Diego, CA (US)

( * ) Notice: Subject to any disclaimer, the term of this patent is extended or adjusted under 35 U.S.C. 154(b) by 84 days.

(21) Appl. No.: 14/052,015

(22) Filed: Oct. 11, 2013

Related U.S. Application Data (60) Provisional application No. 61/712,369, filed on Oct. 11, 2012.

(51) Int. Cl.
  *A61B 17/70* (2006.01)
  *A61B 17/88* (2006.01)

(52) U.S. Cl.
  CPC ......... *A61B 17/7083* (2013.01); *A61B 17/7049* (2013.01)

(58) Field of Classification Search
  CPC ........ A61B 17/7083; A61B 17/7049–17/7052; A61B 2017/00876
  See application file for complete search history.

(56) References Cited

U.S. PATENT DOCUMENTS

| | | | |
|---|---|---|---|
| 4,369,769 A | 1/1983 | Edwards | |
| 4,998,936 A | 3/1991 | Mehdian | |
| 5,049,151 A | 9/1991 | Durham | |
| 5,084,049 A | 1/1992 | Asher et al. | |
| 5,127,913 A | 7/1992 | Thomas, Jr. | |
| 5,154,718 A | 10/1992 | Cozad et al. | |
| 5,505,731 A | 4/1996 | Tornier | |
| 5,514,145 A | 5/1996 | Crickenberger | |
| 5,525,646 A | 6/1996 | Lundgren | |
| 5,545,163 A | 8/1996 | Miller et al. | |
| 5,569,246 A | 10/1996 | Ojima et al. | |
| 5,624,442 A | 4/1997 | Mellinger et al. | |
| 5,669,910 A | 9/1997 | Korhonen et al. | |
| 5,688,272 A | 11/1997 | Montague et al. | |
| 5,797,911 A | 8/1998 | Drewry | |
| 5,810,821 A | 9/1998 | Vandewalle | |
| 5,836,949 A | 11/1998 | Campbell | |
| 5,851,183 A | 12/1998 | Bucholz | |
| 5,947,966 A | 9/1999 | Drewry et al. | |
| 5,980,521 A | 11/1999 | Montague et al. | |
| 5,980,523 A | 11/1999 | Jackson et al. | |
| 6,074,394 A | 6/2000 | Krause | |
| 6,083,226 A | 7/2000 | Fiz et al. | |

(Continued)

FOREIGN PATENT DOCUMENTS

| | | |
|---|---|---|
| EP | 0746255 B1 | 11/2002 |
| EP | 1743585 A1 | 1/2007 |

(Continued)

*Primary Examiner* — Jacqueline Johanas
(74) *Attorney, Agent, or Firm* — Jonathan Spangler; Rory Schermerhorn (57) ABSTRACT

The present invention describes a system suitable for guiding a cross-connector to a target area, such as spinal implants including spinal implant rods, within the body (in vivo) and method of using the same. The system includes a targeting member being constructed of, or having a steering material, which can be coupled to the cross-connector. The system further includes one or more devices which are used to maneuver the targeting member into position prior to attachment of the cross-connector. The cross-connector is traversed into position through the passageway created by the targeting member and secured to one or more spinal implant members.

22 Claims, 11 Drawing Sheets

(56) References Cited

U.S. PATENT DOCUMENTS

| | | | |
|---|---|---|---|
| 6,086,596 A | 7/2000 | Durham | |
| 6,102,912 A | 8/2000 | Cazin | |
| 6,113,600 A | 9/2000 | Drummond et al. | |
| 6,127,597 A | 10/2000 | Beyar | |
| 6,136,003 A | 10/2000 | Hoeck et al. | |
| 6,139,548 A | 10/2000 | Errico | |
| 6,162,228 A | 12/2000 | Durham | |
| 6,168,595 B1 | 1/2001 | Durham | |
| 6,171,311 B1 | 1/2001 | Richelsoph | |
| 6,179,838 B1 | 1/2001 | Fiz | |
| 6,217,578 B1 | 4/2001 | Crozet et al. | |
| 6,226,548 B1 | 5/2001 | Foley | |
| 6,234,705 B1 | 5/2001 | Troxell | |
| 6,236,875 B1 | 5/2001 | Bucholz | |
| 6,238,396 B1 | 5/2001 | Lombardo | |
| 6,283,967 B1 | 9/2001 | Troxell et al. | |
| 6,306,137 B2 | 10/2001 | Troxell | |
| 6,328,740 B1 | 12/2001 | Richelsoph | |
| 6,328,741 B1 | 12/2001 | Richelsoph | |
| 6,331,312 B1 | 12/2001 | Lee | |
| 6,364,885 B1 * | 4/2002 | Kilpela et al. | 606/74 |
| 6,402,751 B1 | 6/2002 | Hoeck et al. | |
| 6,413,258 B1 | 7/2002 | Bernhardt, Jr. | |
| 6,485,491 B1 | 11/2002 | Farris et al. | |
| 6,503,249 B1 | 1/2003 | Krause | |
| 6,524,310 B1 | 2/2003 | Lombardo et al. | |
| 6,530,929 B1 | 3/2003 | Justis | |
| 6,554,832 B2 | 4/2003 | Shluzas | |
| 6,602,253 B2 | 8/2003 | Richelsoph et al. | |
| 6,616,668 B2 | 9/2003 | Altarac et al. | |
| 6,623,484 B2 | 9/2003 | Betz | |
| 6,736,817 B2 | 5/2004 | Troxell et al. | |
| 6,749,614 B2 * | 6/2004 | Teitelbaum et al. | 606/250 |
| 6,752,807 B2 | 6/2004 | Lin et al. | |
| 6,761,721 B2 | 7/2004 | Burgess et al. | |
| 6,783,526 B1 * | 8/2004 | Lin et al. | 606/250 |
| 6,872,208 B1 | 3/2005 | McBride et al. | |
| 6,875,211 B2 | 4/2005 | Nichols et al. | |
| 6,887,241 B1 | 5/2005 | McBride et al. | |
| 6,958,066 B2 | 10/2005 | Richelsoph et al. | |
| 6,960,212 B2 | 11/2005 | Richelsoph et al. | |
| 7,008,422 B2 | 3/2006 | Foley | |
| 7,011,660 B2 | 3/2006 | Sherman | |
| 7,029,474 B2 | 4/2006 | Richelsoph et al. | |
| 7,066,938 B2 | 6/2006 | Slivka et al. | |
| 7,083,622 B2 | 8/2006 | Simonson | |
| 7,104,993 B2 | 9/2006 | Baynham et al. | |
| 7,122,036 B2 | 10/2006 | Vanacker | |
| 7,137,986 B2 | 11/2006 | Troxell et al. | |
| 7,160,301 B2 | 1/2007 | Cordaro | |
| 7,406,775 B2 | 8/2008 | Funk et al. | |
| 7,835,778 B2 | 11/2010 | Foley et al. | |
| 7,976,546 B2 * | 7/2011 | Geist et al. | 606/86 A |
| 8,048,129 B2 * | 11/2011 | Forton et al. | 606/279 |
| 8,092,458 B2 * | 1/2012 | Geist et al. | 606/86 A |
| 8,092,460 B2 * | 1/2012 | Geist et al. | 606/86 A |
| 8,092,461 B2 * | 1/2012 | Geist et al. | 606/86 A |
| 8,317,801 B2 * | 11/2012 | Geist et al. | 606/99 |
| 8,333,771 B2 * | 12/2012 | Geist et al. | 606/86 A |
| 8,366,715 B2 * | 2/2013 | Geist et al. | 606/86 A |
| 8,608,780 B2 * | 12/2013 | Forton et al. | 606/252 |
| RE45,436 E * | 3/2015 | Geist et al. | 606/86 A |
| 2001/0039450 A1 | 11/2001 | Pavcnik | |
| 2002/0052603 A1 | 5/2002 | Nichols et al. | |
| 2002/0143330 A1 | 10/2002 | Shluzas | |
| 2002/0161368 A1 | 10/2002 | Foley | |
| 2002/0169448 A1 | 11/2002 | Vanacker | |
| 2002/0169465 A1 | 11/2002 | Bowman | |
| 2003/0023244 A1 | 1/2003 | Richelsoph et al. | |
| 2003/0065373 A1 | 4/2003 | Lovett | |
| 2003/0153917 A1 | 8/2003 | Richelsoph et al. | |
| 2004/0082954 A1 * | 4/2004 | Teitelbaum et al. | 606/61 |
| 2004/0116928 A1 | 6/2004 | Young et al. | |
| 2005/0038432 A1 | 2/2005 | Shaolian | |
| 2005/0055089 A1 | 3/2005 | Macoviak | |
| 2005/0075562 A1 | 4/2005 | Szakelyhidi, Jr. | |
| 2005/0079088 A1 | 4/2005 | Wirth | |
| 2005/0085714 A1 | 4/2005 | Foley | |
| 2005/0090821 A1 | 4/2005 | Berrevoets et al. | |
| 2005/0171540 A1 | 8/2005 | Lim | |
| 2005/0277934 A1 | 12/2005 | Vardiman | |
| 2006/0041259 A1 | 2/2006 | Paul | |
| 2006/0058789 A1 | 3/2006 | Kim et al. | |
| 2006/0064091 A1 | 3/2006 | Ludwig et al. | |
| 2006/0064093 A1 | 3/2006 | Thramann et al. | |
| 2006/0079894 A1 | 4/2006 | Colleran | |
| 2006/0149135 A1 | 7/2006 | Paz | |
| 2006/0282075 A1 | 12/2006 | Labrom et al. | |
| 2006/0282076 A1 | 12/2006 | Labrom et al. | |
| 2006/0282077 A1 | 12/2006 | Labrom et al. | |
| 2006/0282078 A1 | 12/2006 | Labrom et al. | |
| 2006/0282079 A1 | 12/2006 | Labrom et al. | |
| 2007/0032794 A1 | 2/2007 | Weber | |
| 2007/0083210 A1 * | 4/2007 | Hestad et al. | 606/86 |
| 2007/0167091 A1 | 7/2007 | Schumacher | |
| 2007/0173829 A1 | 7/2007 | Drewry et al. | |
| 2007/0191836 A1 | 8/2007 | Justis | |
| 2007/0191845 A1 | 8/2007 | Justis | |
| 2007/0213714 A1 | 9/2007 | Justis | |
| 2007/0213721 A1 | 9/2007 | Markworth et al. | |
| 2007/0213723 A1 | 9/2007 | Markworth et al. | |
| 2007/0233090 A1 | 10/2007 | Naifeh | |
| 2007/0239159 A1 | 10/2007 | Altarac | |
| 2007/0270808 A1 | 11/2007 | Drewry et al. | |
| 2007/0270809 A1 | 11/2007 | Drewry et al. | |
| 2007/0288009 A1 | 12/2007 | Brown et al. | |
| 2008/0039845 A1 | 2/2008 | Bonutti | |
| 2008/0109039 A1 | 5/2008 | Michielli et al. | |
| 2008/0140100 A1 | 6/2008 | Gertner | |
| 2008/0172093 A1 | 7/2008 | Nilsson | |
| 2008/0177315 A1 | 7/2008 | Usher | |
| 2008/0177323 A1 * | 7/2008 | Null et al. | 606/267 |
| 2008/0312704 A1 | 12/2008 | Hestad | |
| 2009/0048601 A1 * | 2/2009 | Forton et al. | 606/64 |
| 2009/0082666 A1 * | 3/2009 | Geist et al. | 600/424 |
| 2009/0099572 A1 * | 4/2009 | Geist et al. | 606/96 |
| 2009/0131982 A1 * | 5/2009 | Schwab | 606/246 |
| 2009/0287255 A1 | 11/2009 | Erickson | |
| 2010/0049252 A1 * | 2/2010 | Smisson et al. | 606/250 |
| 2010/0234725 A1 * | 9/2010 | Geist et al. | 600/424 |
| 2010/0268338 A1 * | 10/2010 | Melkent et al. | 623/17.11 |
| 2010/0298884 A1 * | 11/2010 | Faizan et al. | 606/266 |
| 2011/0087225 A1 * | 4/2011 | Fritzinger | 606/53 |
| 2011/0238117 A1 * | 9/2011 | Geist et al. | 606/263 |
| 2011/0307020 A1 * | 12/2011 | Geist et al. | 606/86 R |
| 2012/0065691 A1 * | 3/2012 | Simonson | 606/309 |
| 2012/0089187 A1 * | 4/2012 | Forton et al. | 606/250 |
| 2012/0109141 A1 * | 5/2012 | Fritzinger | 606/103 |
| 2012/0179213 A1 * | 7/2012 | Geist et al. | 606/86 A |
| 2012/0179214 A1 * | 7/2012 | Geist et al. | 606/86 A |
| 2014/0100612 A1 * | 4/2014 | Suddaby | 606/273 |
| 2014/0277145 A1 * | 9/2014 | Reitblat et al. | 606/250 |

FOREIGN PATENT DOCUMENTS

| | | |
|---|---|---|
| WO | WO-2006/025919 A2 | 3/2006 |
| WO | WO-2009/105104 A1 | 8/2009 |
| WO | WO-2009/152243 A1 | 12/2009 |

* cited by examiner

SYSTEMS AND METHODS FOR INSERTING CROSS-CONNECTORS

CROSS-REFERENCES TO RELATED APPLICATIONS

This application is a non-provisional patent application claiming the benefit of priority from U.S. Provisional Patent Application Ser. No. 61/712,369 filed on Oct. 11, 2012, the entire contents of which is hereby expressly incorporated by reference into this disclosure as if set forth in its entirety herein.

FIELD OF THE INVENTION

The present invention generally relates to surgical implants; particularly to a system and method for stabilization of adjacent bony structures; and most particularly to a system to help navigate cross-connectors for connecting spinal fixation devices, such as spinal fixation rods, implanted in a patient's spinal system.

BACKGROUND OF THE INVENTION

It is widely held that healing and/or structural correction is greatly facilitated when a bone is stabilized in the proper position. Various devices for stabilization of bone are well known and routinely practiced in the medical arts. For example, an abnormal spine can be stabilized using a substantially rigid or semi-rigid interconnecting means (rod or plate) and fastening means (screws, clamps, hooks, claws, anchors, or bolts). Multiple fasteners are placed into the spinal pedicle of each vertebra and linked by at least one interconnecting means. One of the more difficult aspects is the surgical insertion of the interconnecting means along a fixed path of delivery longitudinally along the vertebrae and through each of the multiple fastening means between multiple vertebrae. Once in place, this system substantially immobilizes the spine and promotes bony fusion (arthrodesis).

Traditionally, the surgical techniques for stabilization of bone required large incisions (upwards of 6 cm in length) and a considerable amount of muscle be cut and stripped away (retracted) from the bone for an "open" visualization of the bone and access thereto for the placement of the fasteners and instrument implantation. Although this so-called "open" surgical technique has successfully treated non-unions, instability, injuries and disease of the spine, it is not without disadvantages. Given the invasive nature of this technique, a lengthy healing time and considerable post-operative pain for the patient is common.

In response to aforementioned drawbacks, the surgical arts have developed minimally invasive systems and procedures intended to replace the more traditional open surgeries. Obviously, a less extensive system and procedure will eliminate the need to perform much of the cutting and stripping of muscle, resulting in reduced recovery time and less post-operative pain. As a result, percutaneous procedures have been developed which insert instruments and perform operations through small skin incisions, usually between 1.5 and 5 cm in length, thereby reducing soft tissue damage. However, smaller skin incisions and smaller surgical fields require more novel and innovative approaches to perform these complicated surgeries.

One such example of a minimally invasive system is the SEXTANT Spinal System by Medtronic (Memphis, Tenn.). This device is comprised of two basic components, screw extenders and the rod inserter, which results in an instrument that looks like a sextant used in naval navigation. The device is an insertion tool that allows fasteners and interconnecting means to be applied to the spine in a minimally invasive manner. The screw extenders are long shafts used to deliver and attach screws to the vertebrae through small skin incisions. During surgery, these extenders protrude outside the body, allowing the surgeon to arrange and join their ends so that the rod inserter may be attached. The rod inserter is an arc-shaped arm that swings along a fixed axis and pushes an interconnecting rod though the skin and muscle and into the heads of the implanted fasteners (pedicle screws).

While the aforementioned technique is adequate when the fastening means are well aligned, it fails to deliver the rod when one of the screws is misaligned. Moreover, the interconnecting rod must be pushed by the surgeon along a fixed arch and cannot be directed around neural structures or bony obstructions. One consequence of forcibly pushing the rod through the fastening means is the possibility of collision between the rod and a bony obstruction causing a piece of bone to break off, resulting in possible neurological damage. Another common problem is the interconnecting rod becoming disengaged from the rod inserter. When either of these incidents happens, additional surgery is often required to remove the bone fragment and rod from the wound. This may result in the surgeon abandoning the minimally invasive approach and reverting to a traditional approach. Current spinal implant systems do not allow the contour of the rod to match the normal curvature of the surrounding anatomy, and such systems are not customizable to meet the individual anatomical variables that each patient presents.

In order to help avoid damaging sensitive anatomy and expedite implant assembly, various image-based navigation systems have been employed which utilize patient images obtained prior to or during the medical procedure to guide a surgeon during the surgery. Recent advances in imaging technology have produced detailed two and three dimensional images using optically guided, fluoroscopic guided, and electromagnetic field based systems. These image-based systems have also been used in combination with the previously described "open" surgeries. One significant problem with most image-based systems is that the radiation generated is transmitted to the patient and surgical staff, which may result in physiological damage over time. Also, the cost and portability of this equipment continue to be an issue. In addition, these systems often require the surgeon undergo extensive training to operate correctly.

Accordingly, a need exists in the surgical arts for a system and minimally invasive procedure capable of providing optimal mechanical support and bony fusion, while reducing the likelihood of bone damage and neural functioning when compared to the currently available interconnecting elements. It is also desirable to provide a surgical procedure that can be performed in conjunction with, but does not require, an image-based tracking system.

DESCRIPTION OF THE PRIOR ART

Although there are numerous patents or patent applications directed to spinal cross-connectors, the prior art nevertheless fails to teach a targeting system for the insertion of spinal cross-connectors using minimally invasive techniques having a decreased risk of causing damage to neural structures or bony obstructions using minimal, if any, radiation exposure to the patient and/or surgeon.

SUMMARY OF THE INVENTION

The present invention is related to previous systems suitable for guiding biocompatible devices, such as surgical rods, to a target area within the body, see for example U.S. application Ser. No. 13/313,765, filed Dec. 7, 2011, entitled "A System For Pushing and Pulling Surgical Implants Into Position In Vivo Via A Tether", application Ser. No. 13/313,528, filed Dec. 7, 2011, entitled "Method and Apparatus for Facilitating Navigation of an Implant", U.S. application Ser. No. 12/728,818, filed on Mar. 22, 2010, entitled "Method and Apparatus For Facilitating Navigation of An Implant", U.S. application Ser. No. 12/157,397, filed on Jun. 10, 2008, entitled "Magnetic Targeting System for Facilitating Navigation", which was issued as U.S. Pat. No. 7,976,546, on Jun. 22, 2011, U.S. application Ser. No. 13/151,756, filed on Jun. 2, 2011, entitled "Magnetic Targeting System For Facilitating Navigation", U.S. application Ser. No. 11/462,592, filed on Aug. 4, 2006, entitled "Magnetic Targeting System and Method of Using The Same", U.S. application Ser. No. 12/338,794, filed on Dec. 18, 2008, entitled "Magnetic Targeting System and Method of Using the Same", each of which are hereby expressly incorporated by reference.

The present invention improves upon the previous applications by providing a system which is adapted for inserting and securing a cross-connector device to spinal rod implants. In one embodiment, the system is adapted to provide a mechanism for direct attachment of the cross-connectors to spinal rod implants secured to a plurality of spinal vertebrae through the use of a plurality of extenders. The extenders are adapted to be securable to the spinal rods and allow for passage of at least a portion of the cross-connector there through. Alternatively, the system in accordance with the present invention can be adapted so that the cross-connector can be secured to the rod using tethering. Accordingly, the present invention includes a targeting member which is attached to a tether. The tether and targeting member are preferably introduced to a target area through an introducer. The introducer, in accordance with the instant invention, includes a mechanism that winds and unwinds the tether allowing the attached targeting member to traverse a distance to the target area, thereby creating a pathway. The system further includes a second winding mechanism positioned at a distance from the introducer. Once the magnetic member reaches its final destination, the tether can be moved in a direction away from the introducer. Attachment of a biocompatible device to the tether allows the biocompatible device to be pulled through the tissue to put the device in place.

Accordingly, it is an objective of the instant invention to provide a system that minimizes soft tissue damage and provides less post-operative pain.

It is a further objective of the instant invention to teach a system for securing a cross-connector to spinal rod implants which allows for shorter surgery, decreased x-ray exposure, and fewer complications for the patient.

It is yet another objective of the present instant to teach a system for securing a cross-connector to spinal rod implants that is simple to operate and reduces the training the surgeon must undergo for operation of peripheral systems.

It is a still further objective of the present invention to teach a targeting system which uses an implant member which is utilized to increase torsional stability of a spinal implant construct.

Other objectives and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

DETAILED DESCRIPTION OF THE INVENTION

While the present invention is susceptible of embodiment in various forms, there is shown in the drawings and will hereinafter be described a presently preferred, albeit not limiting, embodiment with the understanding that the present disclosure is to be considered an exemplification of the present invention and is not intended to limit the invention to the specific embodiments illustrated.

Figure 1:
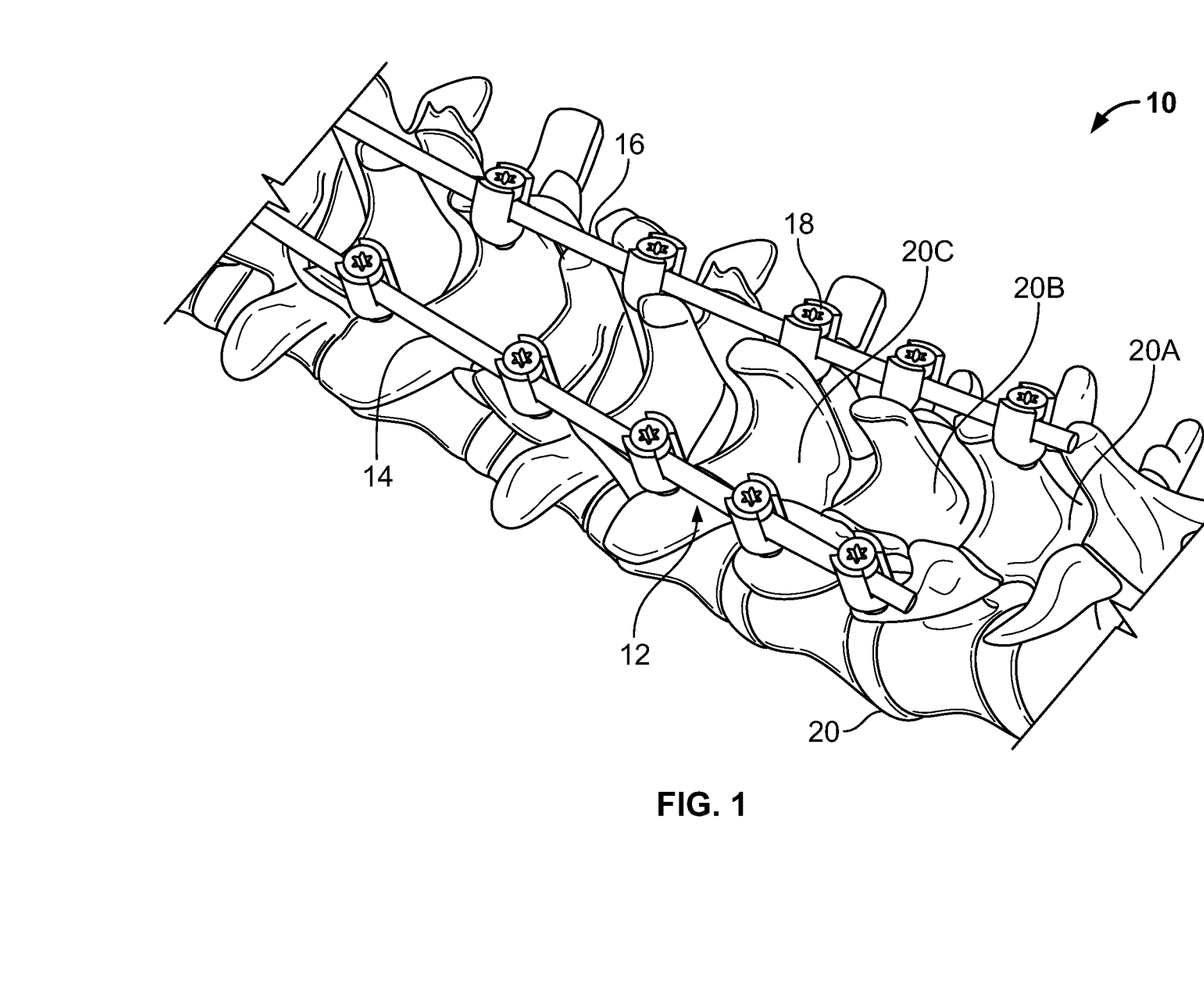
FIG. 1 is a side perspective view of a portion of the human spinal column having spinal implants, illustrated as spinal rods inserted and secured thereto.
Figure 2A:
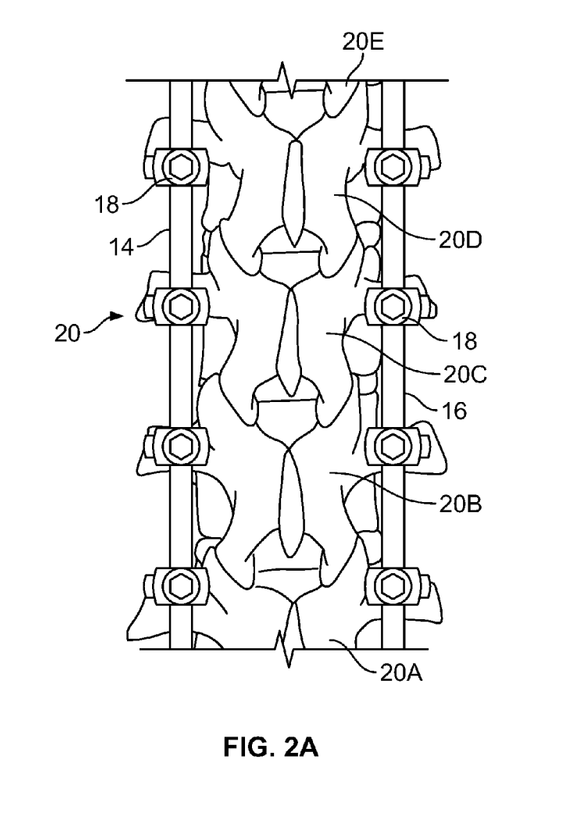
FIG. 2A is a top view of a portion of the human spinal column having spinal implants, illustrated as spinal rods inserted and secured thereto.
Figure 2B:
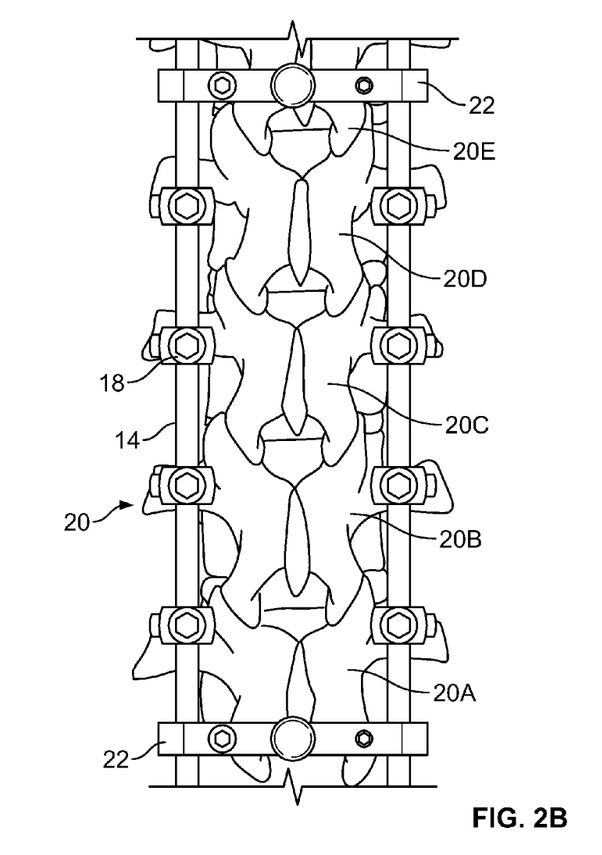
FIG. 2B is a top view of a portion of the human spinal column showing cross-connectors secured to the spinal implant rods.

Referring to FIGS. 1 and 2, partial views of the spinal chord 10 are shown having spinal implants 12, comprising of spinal rods 14 and 16 and spinal rods and anchor members 18, illustrated as pedicle screws. The pedicle screws are secured to portions of several consecutive spinal vertebrae, collectively referred to as 20, individually as 20A, 20B, 20C, etc. One example of a suitable pedicle screw is the multi-axial screw described in U.S. Pat. No. 5,797,911 ('911). Although a multi-axis screw is illustrated in the '911 patent, other screws such as fixed axis screw may be used in the present system as well.

As described in previous Applications by the present inventors, securing of the spinal rods to each individual vertebral body 20 can be accomplished by the system which includes a targeting member (illustrated later) with or without the use of a tether (illustrated later). The tether and targeting member are preferably introduced to a target area through an introducer. The introducer, in accordance with the instant invention, includes a mechanism that winds and unwinds the tether, allowing the attached targeting member to traverse a distance to the target area, thereby creating a pathway. The system further includes a second winding mechanism positioned at a distance from the introducer. Once the magnetic member reaches its final destination, the tether can be moved in a direction away from the introducer. Attachment of a biocompatible device to the tether allows the biocompatible device to be pulled through the tissue and in position to be connected. The system also includes at least one anchoring member constructed and arranged to secure to a target area in vivo at one end.

Figure 3A:
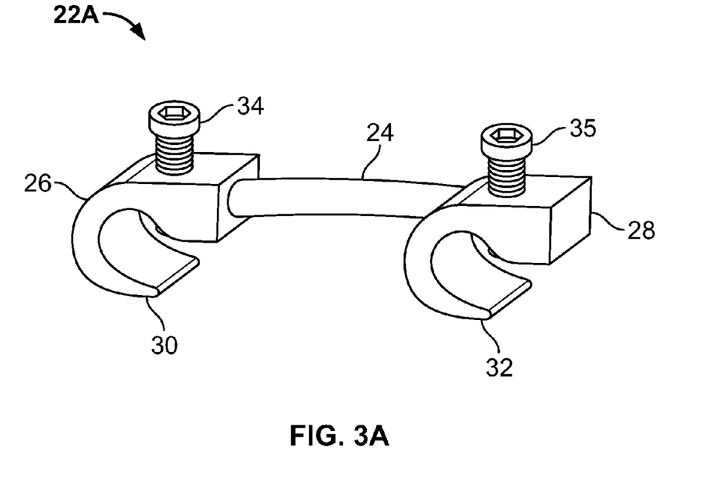
FIG. 3A illustrates an example of a fixed cross-connector.
Figure 3B:
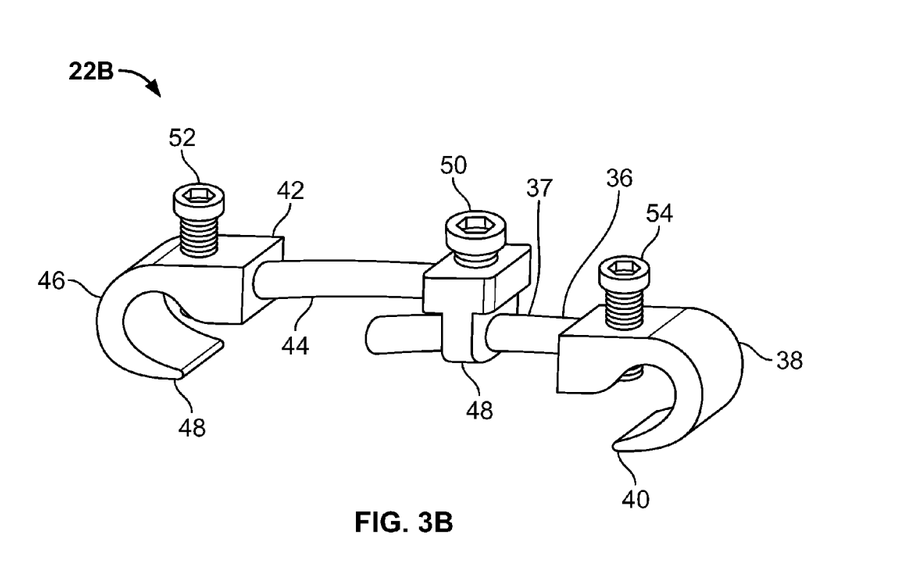
FIG. 3B illustrates an example of a multi-span cross-connector.

In accordance with the present invention, insertion and placement of a cross-connector, referred to generally, without reference to a specific type or configuration, as 22 to spinal implant rods 14, see FIG. 2B, and utilizes a plurality of devices. Cross-connectors are well known in the art, and are used to increase the torsional stability of the spinal implant construct. The cross-connector 22, as used herein, can be based on any cross-connector general construction as known in the art. FIG. 3A illustrates a common fixed type cross-connector 22A. The cross-connector 22A generally has a main body 24 having terminal ends 26 and 28 with spinal rod engaging features, such as hooks 30 and 32. The hooks 30 and 32 are sized and shaped to engage and secure to the spinal implant rods 14 and 16. One or more fastening members, such as screws 34 and 35 are used to secure/unsecure the cross-connector 22A to/from the spinal implant rods 14 and 16. FIG. 3B illustrates an alternative type of cross-connector, the multi-span cross-connector 22B. The multi-span cross-connector 22B contains a first member 36 having a generally tubular structure 37 with first spinal rod engaging feature 38, such as a hook 40. The first member 36 secures to a second member 42. The second member 42 having a generally tubular structure 44 with second spinal rod engaging feature 46, such as a hook 48. The second tubular structure 44 is sized and shaped to engage or secure to the first member 36 through insertion into ring 48. The first member 36 can slide along the second tubular structure 44, providing for adjustable positioning of the first spinal rod engaging feature 38 relative to the second spinal rod engaging feature 46. The exact positioning can be locked in place by securing the screw 50. Additionally, hooks 40 and 38 are secured/unsecured to the spinal implant rods through tightening/loosing of screws 52 and 54.

Figure 4:
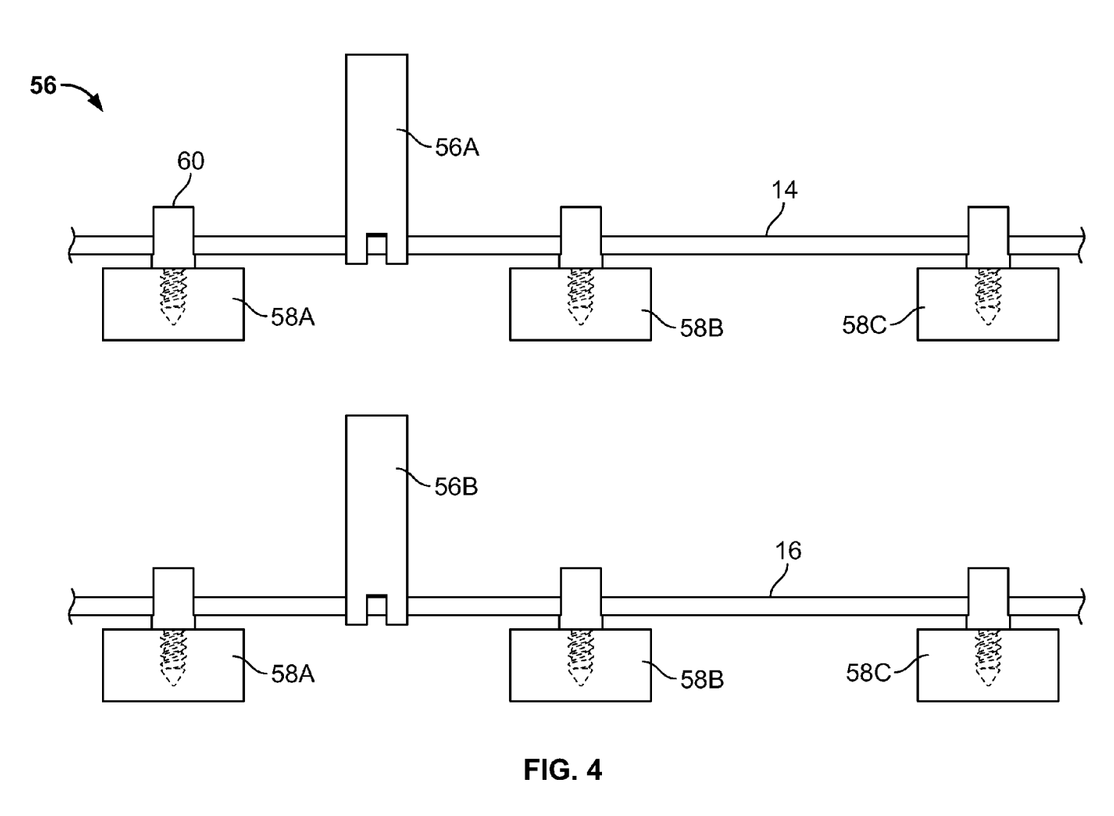
FIG. 4 is a schematic illustration of a system for inserting cross-connectors to spinal fixation devices.

FIG. 4 illustrates the system 56 of the present invention which is suitable for delivering and positioning, i.e. pulling and/or pushing, a cross-connector in vivo, directly or via a tether, wherein like elements are numbered consistently throughout. A plurality of extenders 56A and 56B, collectively referred to as 56, are illustrated. The extenders are shown having a generally tube or cylindrical shape, but may take on other forms. Each extender 56A and 56B is shown coupled to the spinal implant rods 14 and 16. Spinal implant rods 14 and 16 are secured to portions of the individual vertebrae body illustrated as blocks 58A, 58B, and 58C through spinal implant pedicle screws 60.

Figure 5:
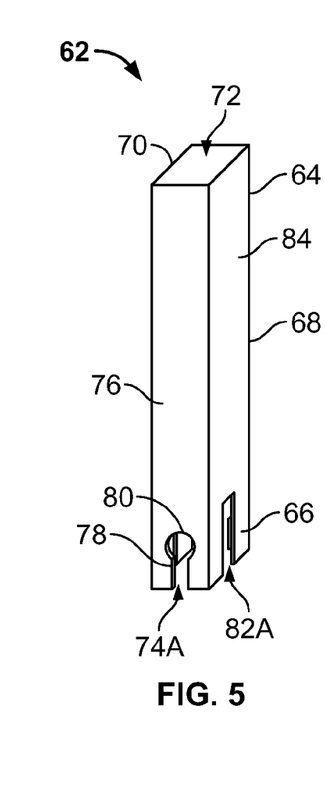
FIG. 5 is a perspective view of an illustrative example of an extender in accordance with the present invention.

FIGS. 5-13 show illustrative examples of extender in accordance with the present invention. Referring specifically to FIGS. 5-9, an extender 62 is shown. The extender 62 is shown having a first end 64, a second end 66, and a main body 68 there between. The main body 68 is illustrated as having a generally rectangular configuration. Such shape, however, is illustrative only and is not intended to be a limiting shape. The first end 64 contains an opening 70 sized and shaped to allow passage of instruments within an internal lumen or passageway 72 spanning the length of the main body 68 between the first end 64 and the second end 66. The second end 66 is constructed and arranged to 1) facilitate removable attachment to spinal implants such as the spinal implant rods 14 or 16, and 2) facilitate delivery of a cross-connector to a position along the rods 14 or 16. To perform such functionality, the second end 66 contains a plurality of spinal implant engaging features along at least two surfaces of the main body. As shown in FIG. 5, a first opening 74A is positioned at the bottom end of surface 76. The first opening 74A is sized and shaped to receive and maintain contact with the spinal implant, such as the spinal implant rod 14.

Figure 6:
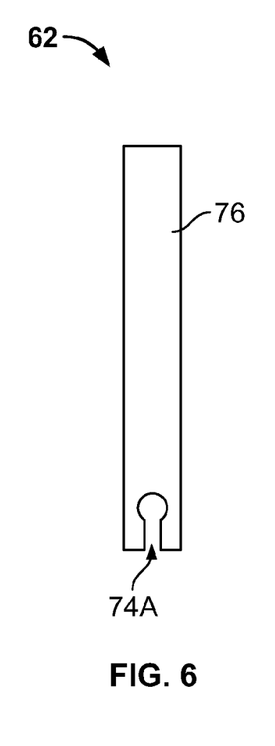
FIG. 6 is a front view of a first side of the extender as shown in FIG. 5.
Figure 7:
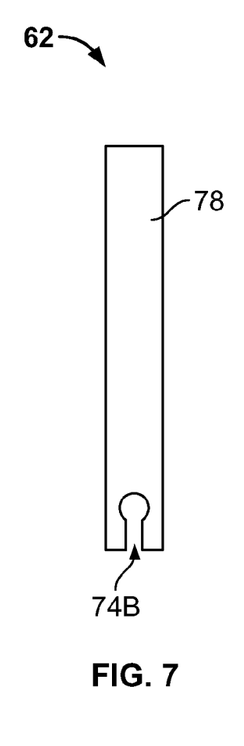
FIG. 7 is a back view of a first side of the extender as shown in FIG. 5.
Figure 14:
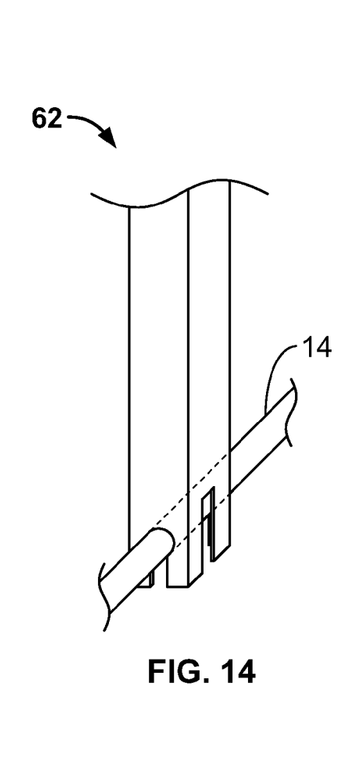
FIG. 14 illustrates the extender as shown in FIG. 5 attached to a spinal implant rod.

While the first opening 74A may be slotted, FIGS. 6 and 7 illustrate the first opening having a key-hole shaped configuration having a narrowed portion 78 and a rounded portion 80. The narrowed portion 78 is sized to allow the cylindrical body of the spinal implant rod 14 to be inserted within. The rounded portion 80 is sized and shaped to receive/engage and secure the cylindrical body of the spinal implant rod 14 to the extender 62, see FIG. 14. The extender 62 preferably contains a second first opening 74B positioned on a second surface 76 which is adjacent to and positioned about 180 degrees from surface 76, see FIG. 7. The second first opening 74B is preferably aligned (i.e. at about 180 degrees separation) with the first opening 74A so that the spinal implant rod 14 or 16 rests within both openings.

Figure 8:
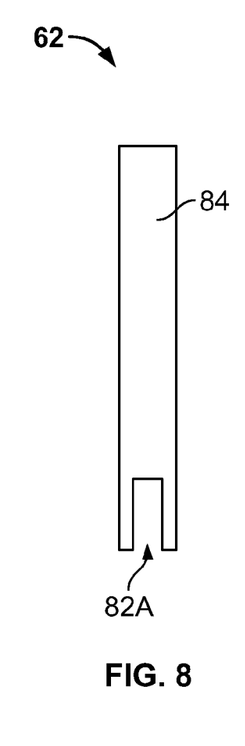
FIG. 8 is a right side view of the extender as shown in FIG. 5.
Figure 9:
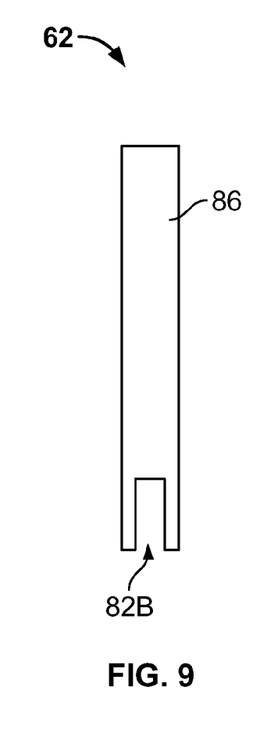
FIG. 9 is a left side view of the extender as shown in FIG. 5.

The extender 62 further contains a second set of openings, second openings 82A and 82B, see FIGS. 8 and 9. The second openings 82A, or 82B, are sized and shaped, such as slotted or other configurations, to allow the cross-connector 22 or other spinal implant devices to pass within or through the extender 62 and aligned with and attachable to the spinal implant rods. The second opening 82A is preferably positioned along a surface 84 of the extender 62 which is at about a ninety degree alignment with surface 76 or 68. Accordingly, the second opening 82A is aligned with the first openings 74A or 74B through about a 90 degree angle. An additional second opening 82B is positioned on a second surface 86 which is adjacent to and positioned about 180 degrees from surface 84, see FIG. 9. The second opening 82B is preferably aligned (i.e. at about 180 degrees separation) with the second opening 82A so that the cross-connector 22 or other spinal implant devices can pass one or both openings.

Figure 10:
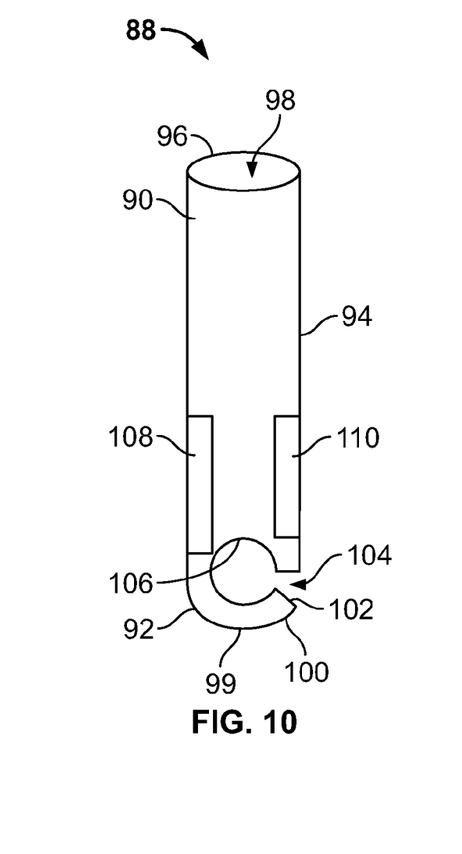
FIG. 10 is a front perspective view of an alternative embodiment of an extender.
Figure 11:
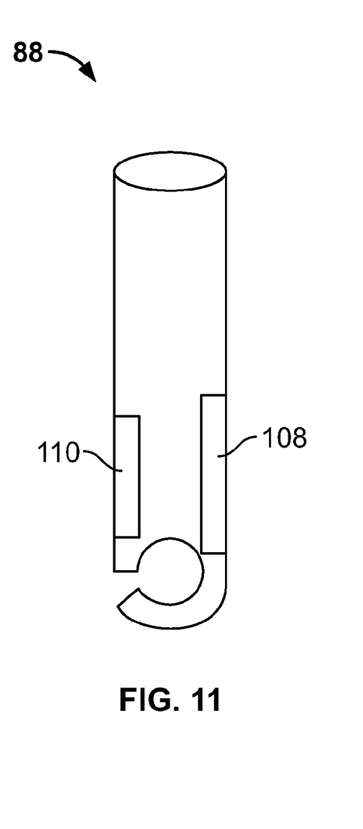
FIG. 11 is a back perspective view of an alternative embodiment of the extender.

FIGS. 10-11 illustrate an alternative embodiment of the extender and are referred to as 88. The extender 88 is shown having a generally tubular shape. Such shape is not intended to be limiting and other shapes, such as the shape described for extender 62 may be utilized. In a similar manner as described for extender 62, the extender 88 has a first end 90, a second end 92, and a main body there between 94.

The first end 90 contains opening 96 sized and shaped to allow passage of instruments within an internal lumen or passageway 98 spanning the length of the main body 94 between the first end 90 and the second end 92. The second end 92 is constructed and arranged to 1) facilitate removable attachment to spinal implants such as the spinal implant rods 14 or 16. To perform such functionality, the second end 92 contains a spinal implant engaging feature. As shown in FIG. 10 and FIG. 11, the second end 92 includes the spinal implant engaging feature illustrated as a hook or J-shaped member 98 sized and shaped to receive/engage and secure to the cylindrical body of the spinal implant rods 14 or 16.

The terminal end 100 of the hook portion 98 may be tapered to aid in the insertion and/or removal of the extender 88 to/from the spinal implant rods 14 or 16. The rod 14 or 16 is positioned within opening 104 and rest along the curved surface 106. The spinal implant engaging feature may be made of a resilient material so that it may flex without failure, i.e. breaking or causing a tear, and return to its original position when the rods 14 or 16 are being inserted or removed. Positioned along the main body 94 are openings 108 and 110. Each opening is sized, shaped, and positioned to facilitate delivery of a cross-connector to a position along the rods 14 or 16.

Figure 12:
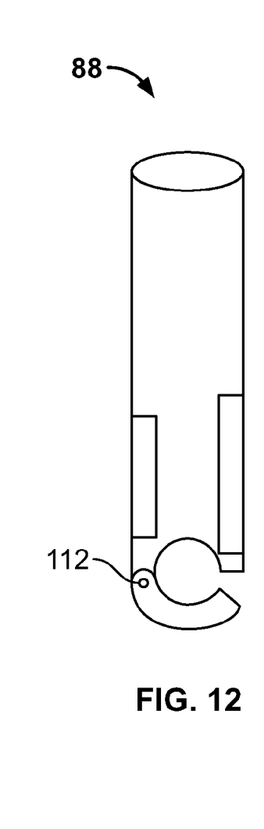
FIG. 12 is a front perspective view of an alternative embodiment of the extender.
Figure 13:
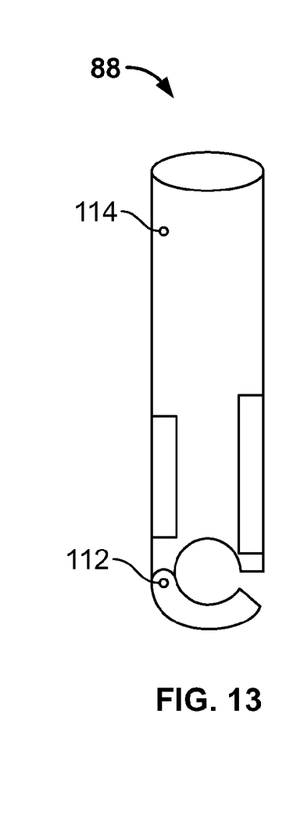
FIG. 13 is a front perspective view of an alternative embodiment of the extender.
Figure 15:
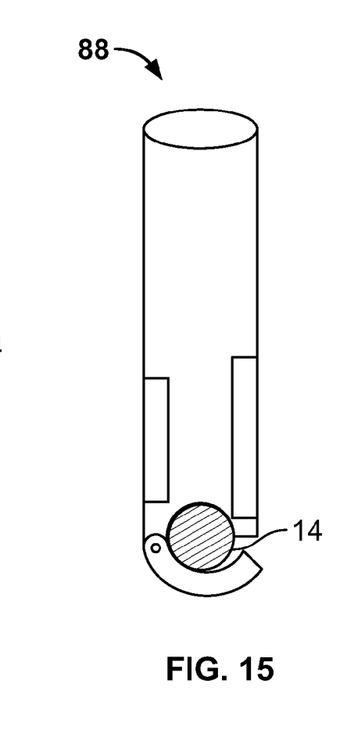
FIG. 15 illustrates the extender as shown in FIG. 10 attached to a spinal implant rod.
Figure 16:
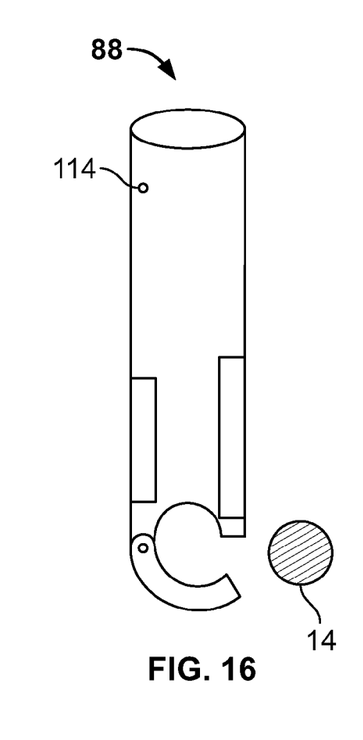
FIG. 16 illustrates the extender as shown in FIG. 13 in the open position.
Figure 17:
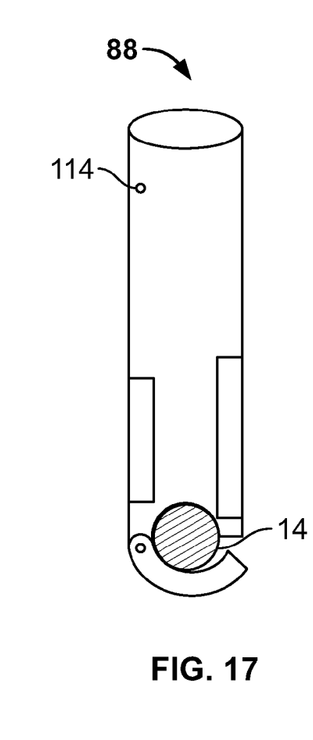
FIG. 17 illustrates the extender as shown in FIG. 13 in the closed position.

Referring to FIGS. 12-13 and 15, an alternative embodiment of the extender 88 is shown. The extender 88 shown in the figure includes a spinal implant engaging feature such as the previously described a hook or J-shaped member 99 which attaches to the seconded end 92 through a hinge 112. The hinge 112 allows for the hook or J-shaped member 99 to easily secure the cylindrical body of the rod 14 or 16 thereto. FIG. 13 illustrates an embodiment of the extender 88 which is designed to allow the user to mechanically manipulate the hook or J-shaped member 99. An actuating device, such as a button 114 mechanically coupled to the hook or J-shaped member 99 is used to manipulate the hook or J-shaped member 99 to traverse from an open position, see FIG. 16, to a closed position, see FIG. 17.

In any configuration, the extenders 62 or 88 should be made of a substantially rigid biocompatible material and have a length dimension that allows the first end 64 or 90 to protrude a distance outside of the percutaneous exposure created through the outer skin of a patient. The interior dimension, 72 or 98 of the extenders 62 or 88 should be such that they are capable of receiving the appropriate driving tool (not shown) used to engage the screws and set screws. In addition, the interior dimension of the extenders should be able to accept a wand or other device for passing various devices, such as a targeting member, including a magnet, a tool such as a magnet or gripping device for removing the targeting member to a location outside of the extender, or the cross-connector itself. In use, each of the first end 64 or 90 of the extenders protrude outside of the patient's skin through percutaneous incisions so that the surgeon is able to insert instrumentation through the extender's interior portion to access the spinal rods 14 or 16 secured to the target area (vertebra). The extenders also enable the surgeon to insert a wand or removal tool into the selected extender to a position proximate a corresponding extender, see FIGS. 19 and 20.

Figure 18A:
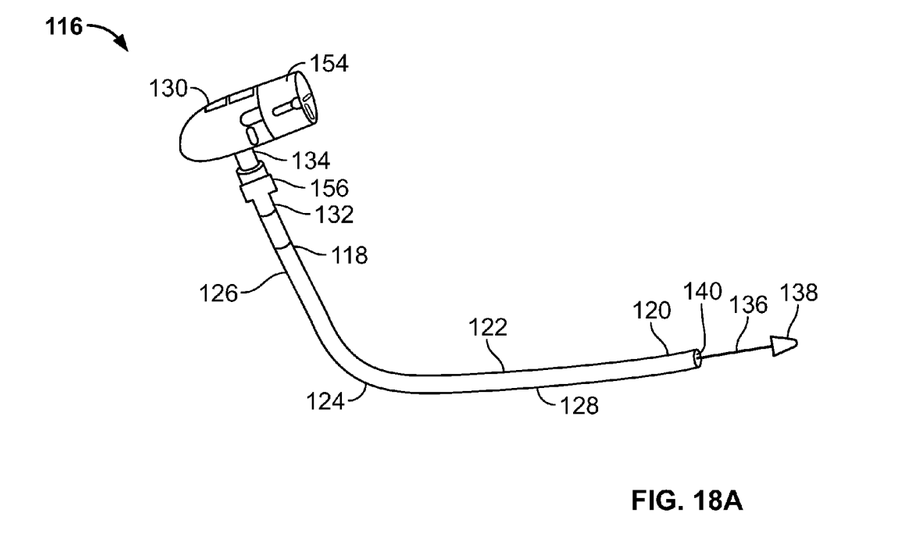
FIG. 18A is a perspective view of an illustrative example of the magnetic introducer that can be used in the system of the present invention.

The system in accordance with the present invention may make use of additional components. For example, a magnetic introducer 116 is used to introduce a targeting member into the system. The magnetic introducer 116 is constructed and arranged to deliver a targeting member to successive extenders 56 without the need for use of visualization techniques such as fluoroscopy. Alternatively, the magnetic introducer 116 may be used to introduce the cross-connector 22 directly to the system. Referring to FIG. 18A, an illustrative example of a magnetic introducer 116 is shown having first end, or proximal end, 118, a second end, or distal end, 120, and an intermediate section 122 there between.

The intermediate section may contain a bend 124 dividing the intermediate section into a generally vertical portion 126 and a generally horizontal portion 128. The intermediate section is made of a material that allows the user the ability to push the intermediate section 122 into place. Removably attached to the proximal end 118 is a handle 130. The handle 130 attaches to a connector 132 through a mateable connector 134 of the handle 130. Alternatively, the handle 130 may be integrally formed as part of the intermediate section. The handle 130 not only provides the user the ability to grab and manipulate the introducer through a space or tissue, but also stores a tether 136 attachable to a targeting member, illustrated herein as a magnetic bullet 138.

The targeting member may be made of a steering material. As used herein, steering material refers to any material capable of being influenced by the magnetic material. For example, the steering material may include any magnetically attractive material or alloy, (e.g. steel, iron, etc). Moreover, the steering material may be coated with any suitable biocompatible element, such as a plastic. The type, shape, and size of the magnetic material and steering material should be suitable for internal use in patients and provide the optimal magnetic field. Magnetic fields are used herein for navigating in vivo since these fields can penetrate human tissue and bone without being distorted similar to x-rays, but without the danger of radiation and physiologic damage. A pre-determined length of the tether 136 is preferably wrapped around a winding/unwinding member, such as a spool, not shown, in a similar manner as a fishing rod reel, so that the tether 136 may traverse the length of the intermediate section 122 of the magnetic introducer 116. The introducer 116 is preferably cannulated such that the targeting member 138 is movable through the distal end opening 140.

Figures 19, 20:
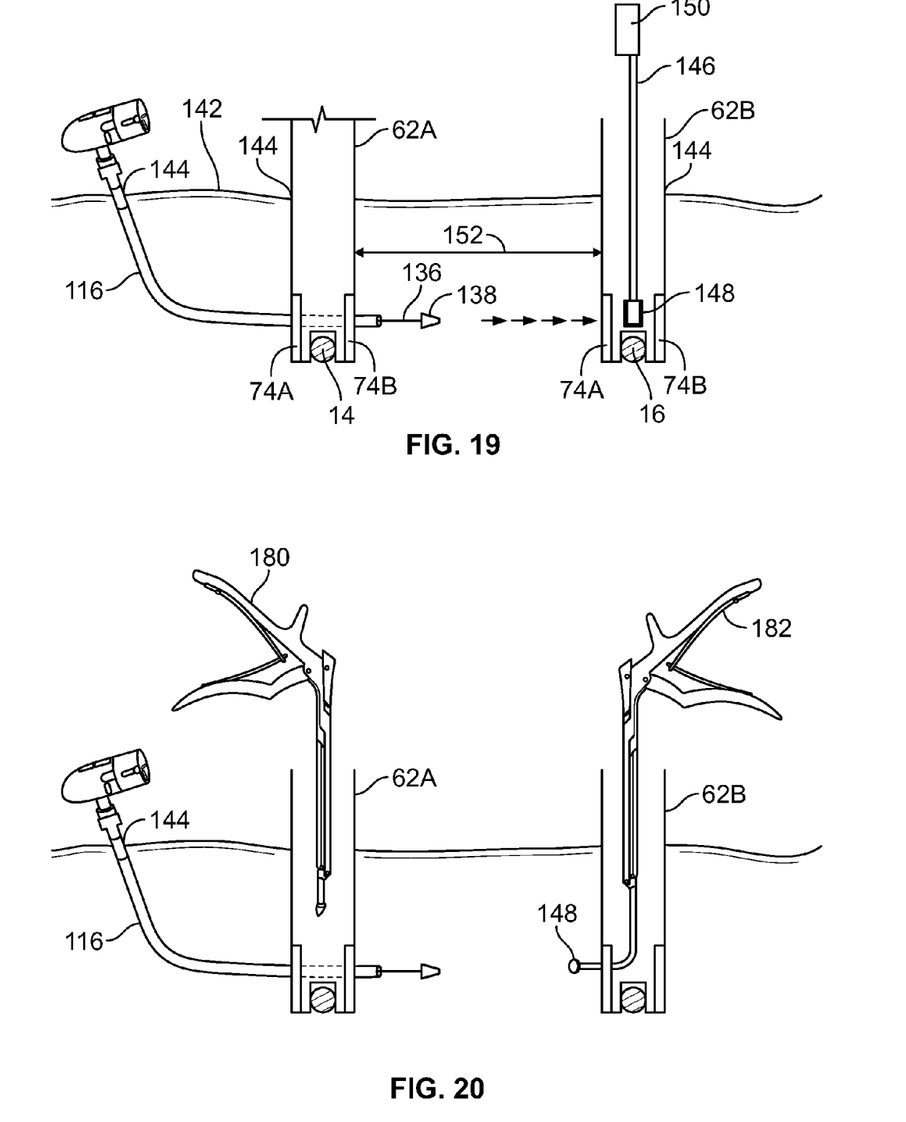
FIG. 19 illustrates use of the introducer and magnetic wands in accordance with the present invention.
FIG. 20 illustrates the use of passer and magnetic catch devices in accordance with the present invention.
Figure 21:
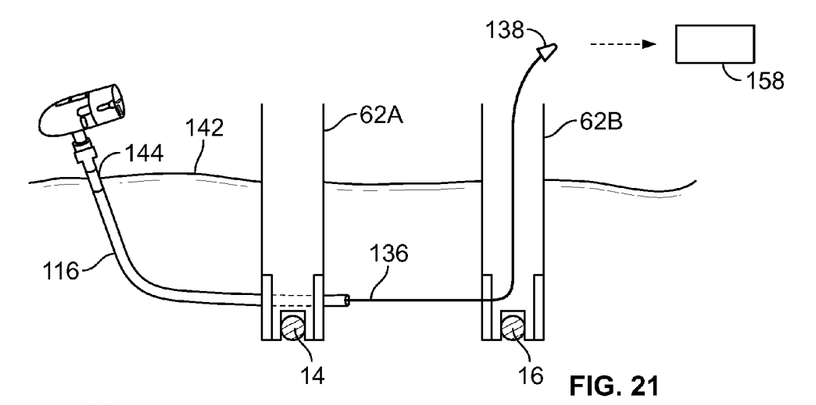
FIG. 21 illustrates the system as shown in FIG. 19, illustrating the targeting member inserted up into and through the second extender.
Figure 22:
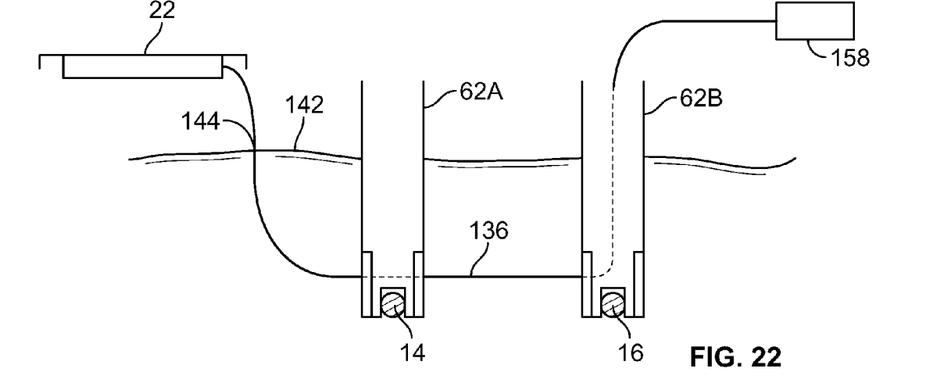
FIG. 22 illustrates the system as shown in FIG. 19, illustrating the coupling of the targeting member/tether to the cable winding device.
Figures 23, 24:
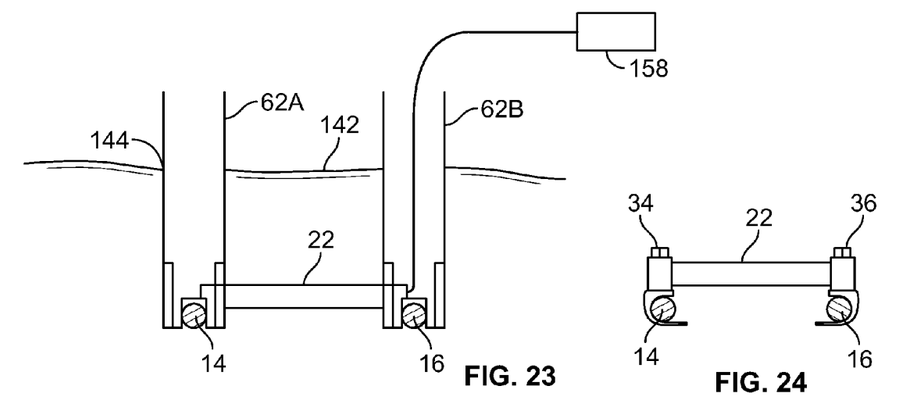
FIG. 23 illustrates the system as shown in FIG. 19 illustrating the aligning of the cross-connector to the spinal implant rods.
FIG. 24 illustrates the system as shown in FIG. 19 with removal of the extenders showing the cross-connector secured to the spinal implant rods.

Referring to FIG. 19, the introducer 116 is shown inserted into a patient so that it extends outside the patient's skin 142 through percutaneous incisions 144 so that the surgeon is able to insert instrumentation there through. The extenders 62A and 62B also extend outside the patient's skin 142 via percutaneous incisions 144 so that the surgeon is able to insert instrumentation there through.

The magnetic introducer 116 is inserted into and through extender 62A via second opening 74A and 74B which are preferably designed to align or rest adjacent to the spinal rod 14 inserted and secured within. A magnetic device, such as a wand 146 having a magnetic material, such as a magnet 148, attached at the distal end thereto and sized to extend the length of the extender, is placed within the extender 62B. Magnetic wands such as those described in U.S. application Ser. No. 13/313,765 or U.S. Pat. No. 7,976,546, Publication Number US 2010-0234725 A1, or Publication Number US 2009-

0082666, and incorporated herein by reference, may be used. The magnetic wand 146 may be designed to employ an electromagnet having controls located in the handle or grip 150. At a minimum, the controls should include buttons and associated circuitry that will allow the surgeon to turn the electromagnet "on" and "off". Preferably, the controls also include buttons and circuitry capable of increasing or decreasing the strength of the magnetic field generated by the electromagnet and/or switch between polarity (north and south poles). As is known, the polarity of a magnet allows it to attract or repel magnetic material within its magnetic field. The controls can also include a display used to indicate the strength of the magnetic field being applied.

Insertion of the magnet 148 creates a force that allows the magnetic bullet 138 of the introducer 116 to traverse the space 152 between spinal rods 14 and 16, entering the extender 62B through opening 74B. As described previously, the magnetic bullet 138 is attached to the tethering member 136. The tethering member 136 therefore, creates a path through the space 152. In addition to the creation of the magnetic field through use of wand 146 which can be turned "on" and "off", the traversal of the magnetic bullet 138 can be controlled through the amount of give and/or tension on the tether 136. For example, in a resting position, the tether 136 may be secured to the handle in such a manner that the magnetic bullet 138 rests at or is extending out of the opening 140 of the distal end 120 of the introducer 116. Even if a magnetic field is applied, there is no slack on the tether 136 to allow the magnetic bullet 138 to move. Turning the knob section 154 of handle 130 in a clockwise direction allows more of the tether 136 to be available so that, as the magnetic field is created, there is enough slack in the tether 136 to allow the magnetic bullet 138 to move. Alternatively, or in addition to, the magnetic introducer may contain a nut 156 which allows the tether 136 to freely freespool, providing enough material for the magnetic bullet 138 to reach its destination. Once the magnetic bullet 138 reaches its destination, the knob 154 can be turned in a counter-clockwise direction to tighten.

Referring to FIGS. 21-24, once the magnetic bullet 138 contacts the magnetic catcher 148, the surgeon can retrieve the magnetic bullet 138 by retracting the wand 146 back up the extender 62B effectively pulling the magnetic bullet 138 out of extender 62B. The magnetic bullet 138 can then be attached to a tether winding device 158 which is used to traverse a cross-connector, which has been connected to the tether at the opposite end of where the tether winding device is to be coupled to the tether, along the path created by the tether 136. The cross-connector 22 can be positioned to the spinal rods 14 and 16 while the extender 62A or 62B remains secured to the rods 14 and 16. Once the cross-connector 22 is moved to the proper place, the surgeon can properly secure the J-shaped ends 30 and 32 to the rod by tightening set screws 34 and 35.

Figure 18B:
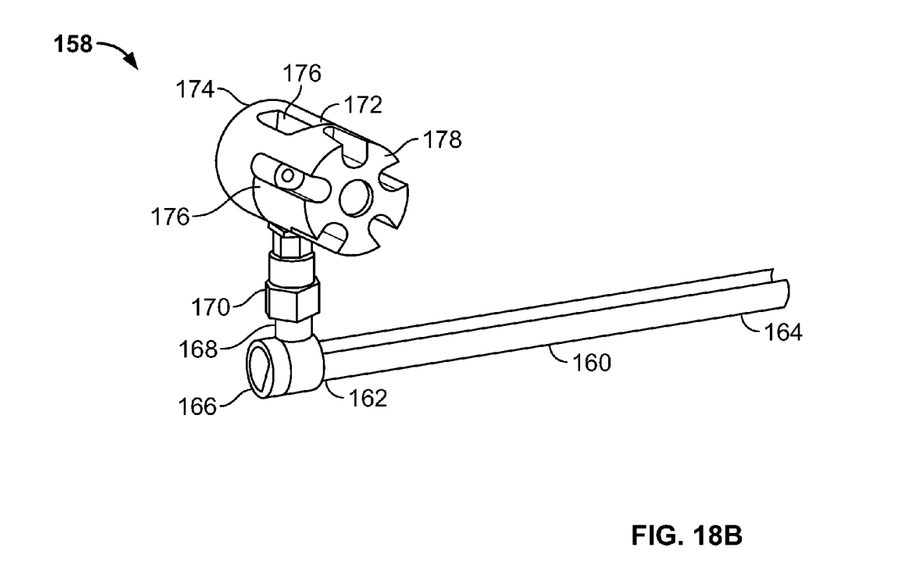
FIG. 18B is a perspective view of an illustrative example of a cable winding device that can be used in the system of the present invention.

Referring to FIG. 18B, an illustrative embodiment of a cable winding device 158 is shown. The cable winding device 158 contains a cannulated tube 160 having a proximal end 162 and a distal end 164. The distal end 164 preferably contains one or more slotted portions (not shown). The proximal end 162 contains opening 166. The opening 166 allows the user the ability to insert one or more surgical devices, such as a retrieval device, into the interior of the cannulated tube 160 to receive the magnetic bullet 138 and pull it up from the distal end 164.

Along the side of the tube 160, near the proximal end 162, is a first connecting member 168 which is mateable with a second connecting member 170. The second connecting member 170 connects a tether winder 172 to the cannulated tube 160. The tether winder 172 contains a main body 174 which is constructed and arranged to receive and store the magnetic bullet 138 and tether 136 within. The tether winder main body may contain one or more slotted portions 176 sized and shaped to receive the magnetic bullet 138. Once placed inside the slotted portion 176, the magnetic bullet 138 may be aligned with a device, such as tether winder reel (not illustrated) which allows the user to turn a rotatable knob 178 to wind the magnetic bullet 138 and tether 136 around the reel. Alternatively, the tether may simply wind around the tether winder main body or the knob 178. The tether winder 172 may further be designed to have a ratchet means wherein turning the knob one revolution at a time in one direction (clockwise) and/or turning the knob one revolution at a time in the opposite direction (counterclockwise) to unwind prevents the unwanted winding and/or unwinding. The tether winder 172 may also be designed to allow the tether to wind/unwind freely without restriction. The cannulated tube 160 may additionally contain a wheel (or other feature, e.g. a cross bar, pin, etc. . . . ) located at the distal end 164, to limit or prevent unwanted movement of the tether, thereby preventing the tether 136 from moving upwardly, towards the proximal end when being tightened or wound.

Figure 18C:
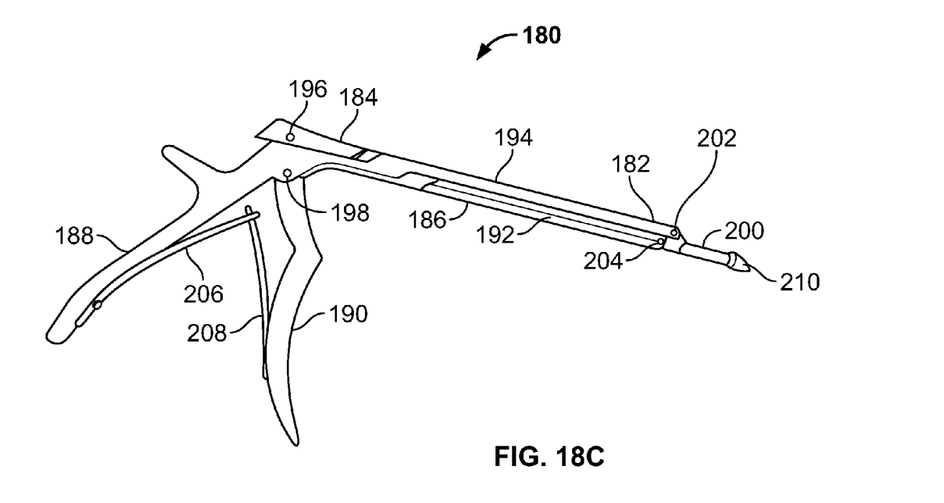
FIG. 18C is a perspective view of the passing device that includes the passing member for the targeting member.

FIG. 19 illustrates alternative methods and instruments for inserting the cross-connector in accordance with the present invention. Each device may utilize a cross-connector that is made entirely, or have a portion thereof, made of a magnetic material. In addition to, or in place of using the introducer 116, a surgeon may utilize a passer device 180 and/or a magnetic catch device 182. Referring to FIG. 18C, the passer device 180 contains a distal end 182, a proximal end 184, and a main body 186 there between. At the proximal end 184 is a hand holding grip 188 and a trigger-like component 190 pivotally attached thereto. The main body 186 may comprise a first elongate rod-like member 192 and a second rod-like member 194 positioned adjacent the first rod-like member 192. The second rod-like member 194 is hingedly connected to the trigger 190 through pivots 196 and 198 at one end, and hingedly connected to a passer member 200 via pivot 202 at the opposite or distal end 182. The passer member 200 is pivotally connected to the first rod-like member 192 at pivot 204. Cantilevered flat springs 206 and 208 are positioned to bias the hand grip 188 and trigger 190 away from one another absent a force exerted by the operator's hand.

In operation, the operator's fingers grip the trigger member 190 and pivotally move in towards the hand grip 188. When springs 206 and 208 abut the trigger and the hand grip, they act against the force exerted by the operator's fingers. The pivotal motion of trigger 190 relative to hand grip 188 results in the relative axial displacement of the first rod-like member 192 with respect to second rod-like member 194. The relative displacement will result in the pivotal movement of passer member 200, via the displacement of pivot 204 with respect to pivot 202. The passer device 180, including passer member 200, is sized to fit within the internal cavity of extenders 12.

Figure 18D:
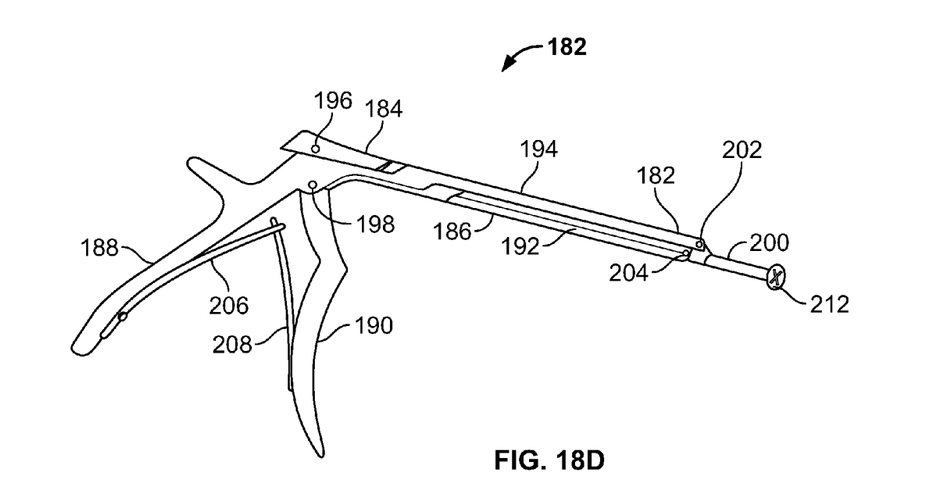
FIG. 18D is an alternative embodiment of the passing device shown in FIG. 18C.

The passer member 200 includes a cross-connector holding portion, such as cavity 210 formed at its distal end which is sized and configured to receive and secure the magnetic bullet 138. The passer 180 may alternatively include claw-like structures which are in operative engagement with the grip 188 and the trigger 190 so that engagement of the trigger 190 results in the claw-like structures moving towards each other. In this configuration, the passer device can be used to grab and hold the magnetic bullet 138. The passer device may also be adapted to act as a retrieval device by replacing the cavity 210 on the passer member 200 with a magnetic catch, such as a magnet 212, designed to attract and firmly secure magnetic bullet 138 to the passer member 200, see FIG. 18D.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A system for coupling a cross-connector to a spinal fixation construct, the spinal fixation construct including first and second bone anchors situated on a first side of the spine and third and fourth bone anchors situated on a second side of the spine, the first and second anchors being coupled together by a first spinal rod and the third and fourth spinal anchors being coupled together by a second spinal rod, the system comprising:

a first extender having a distal end configured to releasably couple to the first spinal rod, a proximal end, a main body having a length extending between the distal end and proximal end, a first pair of openings through the main body adjacent to the distal end, the first pair of openings forming a path through the main body that is transverse to the first spinal rod, and a second pair of openings through the main body adjacent the distal end, the second pair of openings forming a path through the main body that is aligned with the first spinal rod;

a second extender having a distal end configured to releasably couple to the second spinal rod, a proximal end, a main body having a length extending between the distal end and proximal end, a passage spanning the length of the main body, and an opening in the passage adjacent the distal end, a targeting member having a magnetic endpiece and a tether trailing from the endpiece, a magnetic wand advanceable through the passage of the second extender, the magnetic wand having a magnetic field sufficient to attract the magnetic endpiece from a position at the first extender to a position at the second extender, a cross-connector having a leading end with a second engagement feature that is lockable to the second spinal rod and a trailing end with a first engagement feature that is lockable to the first spinal rod and a spanning body connecting the leading and trailing ends, the leading end of the cross-connector being coupleable to the tether such that pulling the tether out through the proximal end of the second extender pulls the cross-connector into position between the two extenders allowing the first end to be locked to the first spinal rod and the second end to be locked to the second spinal rod.

2. The system of claim 1, further including a tether winding device.

3. The system of claim 2, wherein the tether winding device includes a cannulated tube and a spool adjacent a proximal end of the cannulated tube.

4. The system of claim 3, wherein the spool is operated by a knob.

5. The system of claim 3, wherein the tether winding device includes a ratchet mechanism to prevent unwinding of the pool.

6. The system of claim 1, wherein the first extender includes a passage spanning the length of the main body.

7. The system of claim 1, wherein the second extender includes a pair of openings through the main body adjacent the distal end, the openings forming a path through the main body that is aligned with the second spinal rod.

8. The system of claim 1, wherein the magnetic field of the magnetic wand can be turned on and off.

9. The system of claim 8, wherein the magnetic wand includes controls for turning the magnetic field of the magnetic wand on and off.

10. The system of claim 9, wherein the controls are situated in a handle grip of the magnetic wand.

11. The system of claim 9, wherein the controls may also be operated to adjust the strength of the magnetic field.

12. The system of claim 1, wherein each opening of the second pair of openings includes a slot opening in the distal end.

13. The system of claim 12, wherein a proximal portion of each slot is rounded and a distal portion of each slot is narrower than the rounded portion.

14. The system of claim 12, wherein each opening of the first pair of openings includes a slot opening in the distal end.

15. A method for coupling a cross-connector to a spinal fixation construct, the spinal fixation construct having been implanted minimally invasively on a patient's spine and including at least first and second bone anchors situated on a first side of the spine and third and fourth bone anchors situated on a second side of the spine, the first and second anchors being coupled together by a first spinal rod and the third and fourth spinal anchors being coupled together by a second spinal rod, the method comprising the steps of:

advancing a first extender through a minimally invasive exposure to the first spinal rod, the first extender having a distal end configured to contact the first spinal rod, a proximal end, a main body having a length extending between the distal end and proximal end, a first pair of openings through the main body adjacent to the distal end, the first pair of openings forming a path through the main body that is transverse to the first spinal rod, and a second pair of openings through the main body adjacent the distal end, the second pair of openings forming a path through the main body that is aligned with the first spinal rod, advancing a second extender through a minimally invasive exposure to the second spinal rod, the second extender having a distal end configured to contact the second spinal rod, a proximal end, a main body having a length extending between the distal end and proximal end, a passage spanning the length of the main body, and an opening in the passage adjacent the distal end, advancing a targeting member to the pair of openings adjacent the distal end of the first extender, the targeting member having a magnetic endpiece and a tether trailing the magnetic endpiece, advancing a magnetic wand through the passage in the second extender to a position adjacent the opening, activating a magnetic field from the magnetic wand such that the magnetic endpiece of the targeting member is attracted to the magnetic wand and moves between the first extender and second extender to the magnetic wand, the trailing tether forming a path between the first extender distal end and the second extender distal end, pulling the tether through the passage in the second extender to pull a cross-connector attached to a free end of the tether along the path between the between the first extender distal end and the second extender distal end, and locking the cross-connector to the first spinal rod and second spinal rod.

16. The method of claim 15, wherein advancing the targeting member to the pair of openings adjacent the distal end of the first extender comprises advancing the targeting member along a minimally invasive path distinct from the minimally invasive exposures utilized by the first extender and second extender.

17. The method of claim 16, wherein the targeting member is advanced to the first extender with an insertion tool.

18. The method of claim 15, wherein pulling the tether through the passage of the second extender comprises coupling the tether to a winding device and winding the tether.

19. The method of claim 18, wherein the winding device includes a spool around which the tether is wound.

20. The method of claim 19, wherein the spool is a rotatable wheel which is operated to wind the tether around the spool.

21. The method of claim 15, wherein the step of locking the cross-connector to the second spinal rod comprises advancing a tool through the passage in the second extender to operate a locking feature of the cross-connector.

22. The method of claim 21, wherein the step of locking the cross-connector to the first spinal rod comprises advancing a tool through a passage in the first extending to operate a locking feature of the cross-connector.

* * * * *